United States Patent [19]

Johnson

[11] Patent Number: 4,800,885

[45] Date of Patent: Jan. 31, 1989

[54] BLOOD CONSTITUENT MONITORING APPARATUS AND METHODS WITH FREQUENCY DIVISION MULTIPLEXING

[75] Inventor: Eric N. Johnson, Boulder, Colo.

[73] Assignee: The BOC Group, Inc., Montvale, N.J.

[21] Appl. No.: 127,835

[22] Filed: Dec. 2, 1987

[51] Int. Cl.⁴ ............................................... A61B 5/00
[52] U.S. Cl. ...................................... 128/633; 356/41; 364/413.09
[58] Field of Search ........................... 128/633; 356/41; 364/416

[56] References Cited

U.S. PATENT DOCUMENTS 4,653,498  3/1987  New, Jr. et al. ..................... 128/633

FOREIGN PATENT DOCUMENTS 3629447  4/1987  Fed. Rep. of Germany ...... 128/633

*Primary Examiner*—A. Michael Chambers
*Attorney, Agent, or Firm*—Roger M. Rathbun; Larry R. Cassett

[57] ABSTRACT

Apparatus and method for measuring the level of a constituent such as oxygen in the blood of a living subject. Light at a plurality of wavelengths is emitted and directed through the patient's body to a photodetector. The amplitude of the emitted light at each wavelength is varied in accordance with a different carrier frequency, and the photodetector signal thus includes a component at each carrier frequency. Each such component represents transmissivity of the body structure at one wavelength of the emitted light. The photodetector signal is subdivided by frequency so as to separate the components at the different carrier frequencies. The constituent level is determined from these separated components.

19 Claims, 1 Drawing Sheet

BLOOD CONSTITUENT MONITORING APPARATUS AND METHODS WITH FREQUENCY DIVISION MULTIPLEXING

BACKGROUND OF THE INVENTION

The present invention relates to apparatus and methods for monitoring the level of a constituent in the blood of a living organism.

Certain constituents in the blood affect the absorption of light at various wavelengths by the blood. For example, oxygen in the blood binds to hemoglobin to form oxyhemoglobin. Oxyhemoglobin absorbs light more strongly in the infrared region than in the red region, whereas hemoglobin exhibits the reverse behavior. Therefore, highly oxygenated blood with a high concentration of oxyhemoglobin and a low concentration of hemoglobin will tend to have a high ratio of optical transmissivity in the red region to optical transmissivity in the infrared region. The ratio of transmissivities of the blood at red and infrared wavelengths can be employed as a measure of oxygen saturation.

This principle has been used heretofore in oximeters for monitoring oxygen saturation of the blood in the body of a living organism as, for example, in patients undergoing surgery. As disclosed in U.S. Pat. No. 4,407,290, oximeters for this purpose may include red light and infrared light emitting diodes together with a photodetector. The diodes and photodetector typically are incorporated in a probe arranged to fit on a body structure such as an earlobe or a fingertip, so that light from the diodes is transmitted through the body structure to the photodetector. The infrared and red light emitting diodes are switched on and off in alternating sequence at a switching frequency far greater than the pulse frequency. The signal produced by the photodetector includes alternating portions representing red and infrared light passing through the body structure. These alternating portions are segregated by sampling devices operating in synchronism with the red/infrared switching, so as to provide separate signals on separate channels representing the red and infrared light transmission of the body structure. After amplification and low-pass filtering to remove signal components at or above the switching frequency, each of the separate signals represents a plot of optical transmissivity of the body structure at a particular wavelength versus time.

Because the volume of blood in the body structure varies with the pulsatile flow of blood in the body, each such signal includes an AC component caused only by optical absorption by the blood and varying at the pulse frequency or heart rate of the organism. Each such signal also includes an invariant or DC component related to other absorption, such as absorption by tissues other than blood in the body structure. According to well known mathematical formulae, set forth in said U.S. Pat. No. 4,407,290, the oxygen saturation in the blood can be derived from the magnitudes of the AC and DC components of these signals.

As also set forth in the '290 patent, the same general arrangement can be employed to monitor constituents of the blood other than oxygen such as carbon dioxide, carbon monoxide (as carboxyhemoglobin) and/or blood glucose, provided that the other constituents have some effect on the optical properties of the blood.

Measurement apparatus and methods of this type have been widely adopted in the medical profession. However, the signal sampling devices must be precisely synchronized with the switching devices used to provide the alternating rods and infrared illumination. The circuitry required to maintain this synchronization adds cost and complexity to the apparatus. Moreover, the signals representing light transmission at each wavelength are necessarily discontinuous.

Moreover, such apparatus and methods have been subject to interference from ambient light falling on the photodetector. The devices used to recover the meaningful signal components after amplification of the photodetector signal have been provided with circuits for canceling components caused by ambient light. Generally, these circuits operate by obtaining a "dark current" signal representing the amplified photodetector signal during intervals when both of the light emitting diodes are off and hence all of the light falling on the photodetector represents ambient light. The dark current signal value can be used to cancel the ambient light component in signals representing infrared and red light.

This approach provides only a partial solution to the ambient light interference problem. The dark current cancellation circuitry adds complexity and cost to the apparatus. Also, the ambient light signals may saturate or overload the initial or front end amplifier connected to the photodetector, resulting in unpredictable fluctuations in the amplifier output. To prevent saturation of the front end amplifier, its gain may be limited, but this in turn requires higher gain in subsequent stages, more amplification stages or both. Baffles can be used to limit ambient light reaching the photodetector, but these add further complexity and cost, and are only partially effective.

Electromagnetic interference capacitively or inductively coupled to the photodetector and/or leads can also saturate the front end amplifier or create spurious signals. The shielding used to protect the photodetector and leads from this interference adds further cost, complexity and bulk.

A new solution to the problems of electromagnetic and ambient light interference is set forth in the copending, commonly assigned United States patent application of Alan Dean Martin entitled "Blood Parameter Monitoring Apparatus and Methods", filed on the same day as the present application. The disclosure of said application of Martin is incorporated by reference herein. As disclosed in said application of Martin, the light emitted by the illuminating means such as a light emitting diode is varied at one or more carrier frequencies. Therefore, the photodetector signal will include one or more components at the carrier frequency or frequencies, and these components will represent the light transmitted through the patient's body structure from the light emitting means. Modification means are provided for modifying the photodetector signal, preferably prior to any amplification, so as to increase the ratio of the carrier frequency component or components to other components of the signal. Typically, the modification means include a filter such as a passive resonant circuit, resonant at the carrier frequency or frequencies employed. The resonant circuit is arranged to pass only signal components at the carrier frequency or frequencies, while substantially attenuating other components. The modification means effectively eliminates both components of the signals due to ambient light, and also effectively eliminates typical electromagnetic interference signals. Thus, the front end amplifier cannot be overloaded by these spurious signal components. Also, because the ambient light components are effectively eliminated by the modification means, the device need not incorporate separate "dark current" compensation circuitry.

The preferred apparatus set forth in the aforementioned Martin application, however, utilizes a time division multiplexing scheme. Thus, light of different wavelengths is applied in a sequence of alternating bursts at a predetermined switching frequency, with the light within each burst varying in amplitude at the carrier frequency or frequencies. The modified photodetector signal from the modification means or resonant circuit is sampled at predetermined times corresponding to the alternating bursts of light at the different wavelengths, so that the sampling procedure effectively separates signals representing transmissivity at each wavelength. This arrangement thus requires switching, sampling and timing circuitry.

Accordingly, there have been significant needs heretofore for still further improvements in blood constituent monitoring apparatus such as medical oximeters.

SUMMARY OF THE INVENTION

The present invention provides apparatus and methods which address these needs.

Apparatus according to one aspect of the present invention includes illumination means for emitting light at a plurality of wavelengths and directing the emitted light through a body structure. Photodetector means are provided for receiving light transmitted from the illumination means through the body structure and producing one or more photodetector signals representing the intensity of the transmitted light. The illumination means and photodetector means may include, respectively, light emitting diodes and a photodiode.

Carrier frequency means are provided for varying the intensity of the light of each wavelength emitted by the illumination means at a different carrier frequency so that a separate carrier frequency is associated with each wavelength. As the light of each wavelength emitted by the illumination means and transmitted through the body varies at the associated carrier frequency, the photodetector signal or signals will also include components at the different carrier frequencies. The component of the photodetector signal at each carrier frequency will represent light of the associated wavelength transmitted through the body structure. Thus, the component at each carrier frequency will bear information relating to the optical absorptivity or transmissivity of the body structure at the associated wavelength emitted by the light emitting means. Typically, the amplitude of the component at each carrier frequency will vary in accordance with the transmissivity of the body structure at the associated wavelength.

Separation means are provided for subdividing the photodetector signal or signals by frequency so as to separate the components at the different carrier frequencies from one another. Such separation of the different carrier frequency components serves to separate the signals representing transmissivity at the different wavelengths. Interpretation means are provided for determining the level of the blood constituent to be monitored from the separated signals. Because the signals representing transmissivity at the different wavelengths are separated according to their respective carrier frequencies, the time division multiplexing arrangements heretofore utilized can be eliminated. According to preferred aspects of the present invention, the illumination means emits light of all of the different wavelengths simultaneously. Light of each wavelength may be emitted substantially continuously during the measurement operation, subject only to the repetitive amplitude or intensity variations imposed by the carrier frequency means.

Preferably, the separation means includes a plurality of filters, one for each carrier frequency, and each such filter is arranged to provide a filtered output signal consisting principally of the signal component at the associated carrier frequency. Thus, the filters serve to reject ambient light and electromagnetic interference signals in addition to separating the different carrier frequency components from one another. According to the broad compass of the invention, the separation means can act on the photodetector signal either before or after that signal has been preliminarily amplified or otherwise processed. Preferably, however, the filters in the separation means are connected between the photodetector means and the initial amplification stage. Thus, the filters receive the photodetector signal or signals directly from the photodetector means without prior amplification. Separate amplifiers are associated with the individual filters so that each amplifier receives the output signal from one such filter, and hence receives the signal component at one carrier frequency. In this arrangement, the filters prevent overloading of the front end amplifiers by spurious signal components. Although active or passive filters may be employed, passive filters are preferred, and each filter preferably incorporates an inductive/capacitive network. Preferably, tuning means are provided for adjusting the carrier frequency means, the filters or both to match the carrier frequencies with the resonant frequencies of the filters.

The interpretation means typically includes separate signal processing channels, each associated with one carrier frequency and hence with one wavelength. Each such channel typically incorporates means for demodulating the carrier frequency signal so as to recover a base band or unmodulated signal representing the variation in transmissivity at the associated wavelength versus time. Appropriate means are provided for recovering the AC and DC components of each such baseband signal. The interpretation means preferably also includes means for computing the level of a constituent in the blood from the AC and DC components of the transmissivity signals for the different wavelengths.

Further aspects of the present invention include methods of monitoring the level of a blood constituent. These methods preferably employ steps corresponding to the functions described above.

These and other objects, features and advantages of the present invention will be more readily understood from the detailed description of the preferred embodiments set forth below taken in conjunction with the accompanying drawing.

DETAILED DESCRIPTION OF THE PREFERRED EMBODIMENTS

Figure 1:
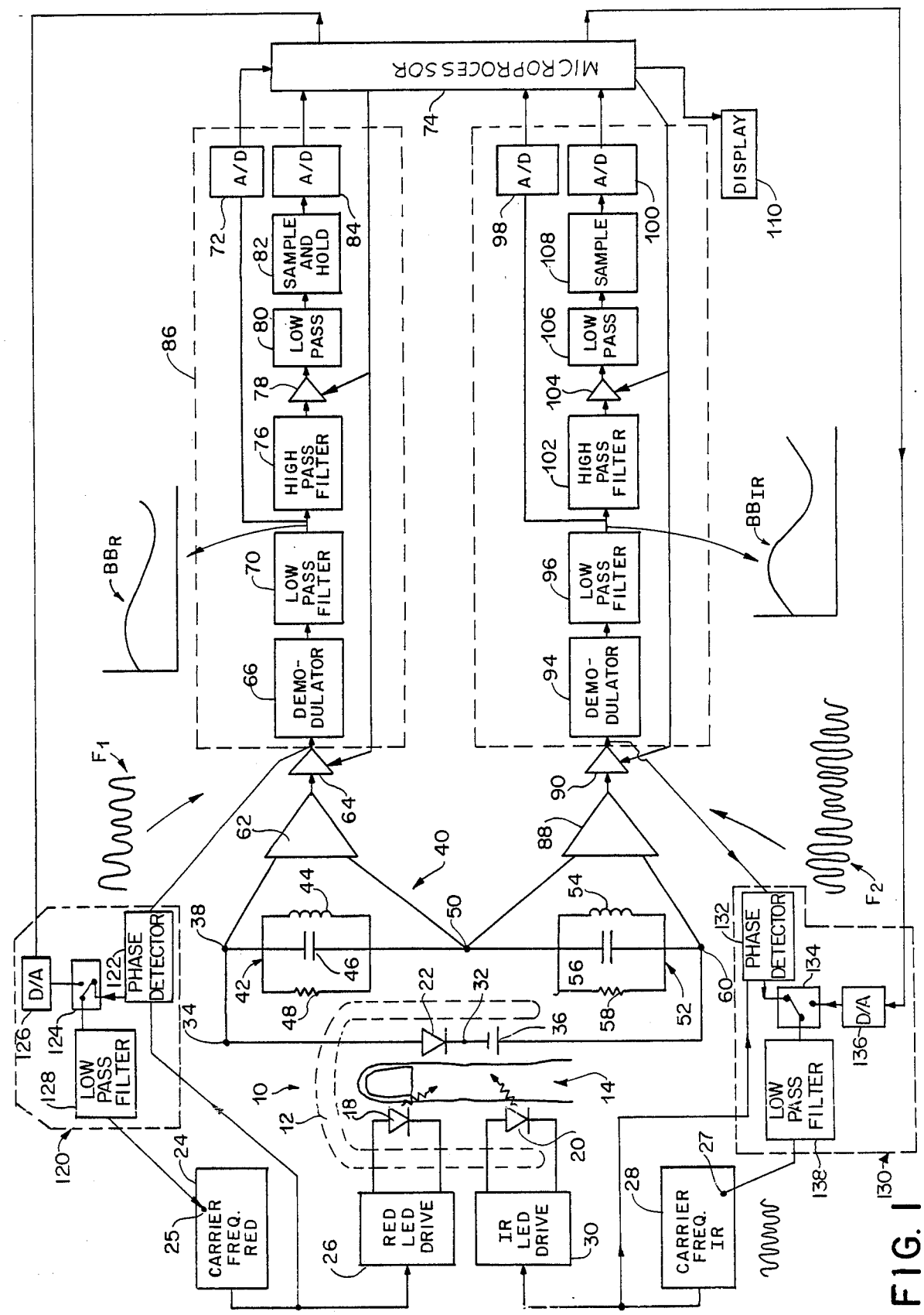
FIG. 1 is a schematic view of apparatus according to one embodiment of the present invention together with certain waveforms utilized therein.

Apparatus according to one embodiment of the present invention includes a probe 10 incorporating a clip 12 adapted to mount on a body structure such as a fingertip 14. Light emitting means including a red light emitting diode or "LED" 18 and an infrared light emitting diode 20 are mounted to clip 12. A photodetector 22, which in this case is a photodiode, is also mounted to clip 12. These components are arranged so that when the clip 12 is secured to the body structure, light from the LED's 18 and 20 will be directed through the body structure to impinge upon the photodiode 22.

A first carrier frequency generator 24 is arranged to provide a substantially continuous signal at a first carrier frequency within a first frequency range. Carrier frequency generator 24 is responsive to a control signal applied at an input 25 to adjust the first carrier frequency within the first frequency range. Carrier frequency generator 24 is connected to a red LED drive circuit 26, which in turn is connected to red LED 18. The carrier frequency generator 24 and drive circuit 26 are arranged so that the power applied by drive circuit 26 to LED 18, and hence the intensity of the light emitted by LED 18 will vary in accordance with the carrier frequency signal. Thus, the intensity of the red light will repeatedly increase and decrease at the first carrier frequency.

A second carrier frequency generator 28 is connected to an infrared LED circuit 30, which in turn is connected to infrared light emitting diode 20. These components are similar to first carrier frequency generator 24 and red LED drive circuit 26 respectively. However, second carrier frequency generator 28 is arranged to operate within a second carrier frequency range different from the first frequency range, and to adjust the second carrier frequency within this second range responsive to a control signal applied at an input 25. The intensity of the infrared light emitted by LED 20 will vary at the second carrier frequency. Because the first and second frequency ranges utilized by carrier frequency generators 24 and 28 do not overlap, the first and second carrier frequencies will differ from one another.

Photodiode 22 has an input node 32 and an output node 34. The input node of the photodiode is connected to a bias voltage source 36 which maintains the diode in a reverse biased condition. The output node 34 of the diode is connected to the a node 38 of a filter network 40.

Filter network 40 incorporates a first resonant circuit or filter 42 including inductor 44, capacitor 46 and damping resistor 48, all of which are connected in parallel between node 38 and a midpoint node 50. Filter network 40 also includes a second, generally similar resonant circuit or filter 52 composed of inductor 54, capacitor 56 and damping resistor 58, these components being connected in parallel between midpoint node 50 and a ground node 60.

The values of inductor 44, capacitor 46 and damping resistor 48 establish the resonant frequency of first resonant circuit 42, and also establish the width of the passband of the first resonant circuit extending above and below its resonant frequency. Inasmuch as the inductor, capacitor and resistor values are subject to finite tolerances, the resonant frequency is subject to a finite tolerance. However, the component values and tolerances are selected so that the resonant frequency of the first resonant circuit is within the first frequency range associated with red carrier frequency generator 24. Also, the passband of circuit 42 is encompassed within the first frequency range. The passband of circuit 42 thus substantially excludes the second frequency range associated with IR carrier frequency generator 28. Conversely, second resonant circuit or filter 52 has a resonant frequency within the second frequency range associated with generator 28, and a passband extending slightly above and slightly below this resonant frequency. The passband of second resonant circuit 52 substantially excludes the first frequency range. Where the signals applied to filter network 40 include a composite of signals at many different frequencies, the first filter output signal appearing between nodes 38 and 50 will consist essentially of voltage signals at frequencies within the passband of filter 42. Signals at other frequencies are shunted between these output terminals and hence do not appear as voltages across nodes 38 and 50. The output signal appearing as a voltage between nodes 50 and 60 will consist essentially of frequencies within the passband of the second filter 52.

A first differential amplifier 62 is connected across the output nodes 38 and 50 of first filter 42. Amplifier 62 is arranged to deliver an output voltage substantially proportional to the voltage appearing between nodes 38 and 50. A first intermediate amplifier 64 is connected to the output of amplifier 62, the output of intermediate amplifier 64 being connected to the input of a demodulator 66. Demodulator 66 per se may be a conventional AM demodulating circuit of the type normally utilized to recover audio frequency or sub-audio frequency baseband signals form an amplitude modulated signal. For example, demodulators of the types normally utilized in AM radio reception can be employed. Alternately, demodulator 66 may be a sampling device arranged to take successive, very brief samples of the signal from intermediate amplifier 64 at times coordinated with the peaks in the first carrier frequency signal from generator 24. The output of demodulator 66 is connected to the input of a low pass filter 70 having a top cutoff frequency of about 10 Hz, filter 70 being arranged to pass signal components below this frequency and to substantially attenuate signal components above the cutoff frequency. The output of low pass filter 70 is connected to an analog to digital converter 72, which in turn is connected to a microprocessor 74. The output of low pass filter 70 is also connected to the input of a high pass filter 76. High pass filter 76 is arranged to attenuate frequencies below about 0.5 Hz and to pass frequencies above that value. The 0.5 Hz value represents the "corner" frequency of the high pass filter, i.e., the frequency at which the filter provides about 3 db attenuation. Frequencies below about 0.5 Hz are attenuated to a greater degree. The output of high pass filter 76 is connected to an amplifier 78, referred to herein as a "channel amplifier", and the output of channel amplifier 78 is connected to a low pass filter 80, having a corner or 3 db attenuation frequency of about 10 Hz. The output of low pass filter 80 is connected to a sample and hold device 82, which in turn is connected to an analog to digital converter 84. The analog to digital converter 84 is connected to microprocessor 74. The components connected between amplifier 64 and the microprocessor constitute a first signal processing channel 86.

The apparatus also includes a second differential amplifier 88 having its input terminals connected to the output nodes 50 and 60 of the second filter or resonant circuit 52. The output of amplifier 88 is connected to a second intermediate amplifier 90 which in turn is connected to a second signal processing channel 92. Amplifiers 88 and 90 are substantially similar to amplifiers 62 and 64 respectively, whereas the second signal processing channel 92 is substantially similar to the first signal processing channel 86. Thus, second channel 92 includes a demodulator 94, low pass filter 96, analog to digital converters 98 and 100, high pass filter 102, channel amplifier 104, low pass filter 106 and sample and hold unit 108. These components are substantially similar to the corresponding components of the first signal processing channel 86.

The microprocessor 74 is arranged to receive digital voltage values or representations from the various analog to digital converters. As explained hereinbelow, the microprocessor is adapted to determine the level of oxygen in the patient's blood from these values. Also, the microprocessor 74 is connected via feedback connections, indicated in broken lines in FIG. 1, to each of intermediate amplifiers 64 and 90 and to channel amplifiers 78 and 104. Via these feedback connections, the microprocessor 74 can control the gain of each of these amplifiers. The microprocessor 74 is also connected to a display unit 110 so that the calculated oxygen value from the microprocessor is displayed on unit 110.

A tuning circuit 120 is associated with red carrier frequency generator 24 and with first resonant circuit 40. Tuning circuit 120 includes a phase detector 122 having one input connected to the output of intermediate amplifier 64 and another input connected to the output of first or red carrier frequency generator 24. Phase detector 122 is arranged to provide a control signal varying with the difference in phase between the signals applied at its two inputs. The output of phase detector 122 is connected to one input terminal of a switch 124, whereas another input terminal of the switch is connected to the output of a digital-to-analog converter 126. Converter 126 in turn is connected to microprocessor 74. Switch 124 is controlled by microprocessor 74 to feed signals from converter 126 or detector 122 to the input of a low pass filter 128. The output of filter 128 is connected to the control input 25 of first carrier frequency generator 24.

A similar tuning circuit 130 is associated with the second or IR carrier frequency generator 28 and second resonant circuit 52. Tuning circuit 130 includes a phase detector 132, switch 134, digital-to-analog converter 136 and low pass filter 138 substantially identical to the corresponding components of circuit 120. The inputs of phase detector 132 are connected to the outputs of intermediate amplifier 90 and of second carrier frequency generator 28. The output of low pass filter 138 is connected to the control input 27 of generator 28.

In a method according to one embodiment of the present invention, clip 12 is mounted to the fingertip 14 of a human patient. Carrier frequency generator 24, red LED drive 26 and red LED 18 are operated so that LED 18 substantially continuously emits red light with its intensity varying at a first carrier frequency within the first range. Likewise, carrier frequency generator 28, IR LED drive 30 and IR emitting LED 20 are actuated to emit infrared light substantially continuously but with its intensity varying at the second predetermined carrier frequency. Apart from the variations in intensity at the carrier frequencies, the intensity of the red and infrared light is substantially constant. The light from diodes 18 and 20 passes through the fingertip to the photodiode 22. As the light passes through the fingertip, portions of the liguht are absorbed and only the remainder is transmitted to photodiode 22. Thus, the red and infrared light passing through the fingertip will be amplitude-modulated in accordance with the red and infrared transmissivities of the fingertip respectively. The transmissivity at each wavelength will vary with the specific optical absorbtivity of the blood at that wavelength and hence with the oxygen concentration in the blood. The transmissivity at each wavelength will also vary with the amount of blood in the patient's fingertip and hence with the patient's pulse.

The conductance of photodiode 22 will vary substantially instantaneously in accordance with the total intensity of all light impinging on the photodiode. The light impinging upon the photodiode will include both the red and infrared light transmitted through the patient's fingertip, in addition to some ambient light. The ambient light typically will include a constant or DC component together with a flicker frequency component, typically at about 100–120 Hz. The conductance of the photodiode, and hence the photodetector output signal appearing at node 34 thus will include a component at the first carrier frequency, the amplitude of the this component varying in accordance with the red wavelength transmissivity of the fingertip, and also will include a corresponding component at the second carrier frequency, the amplitude of this component varying with the infrared transmissivity. In addition, the photodetector output signal will include DC and flicker frequency components representing ambient light. The signal may also include components at other frequencies representing electromagnetic interference and the like.

As the photodetector output signal is applied to filter network 40, the filtered output signal or voltage appearing between nodes 38 and 50 corresponds essentially to only those components of the photodetector output signal within the passband of the first resonant circuit or filter 42. The filtered output signal is amplified by front end amplifier 62 and by intermediate amplifier 64.

Because of the tolerances in the resonant circuit components, there may be some mismatch between the first carrier frequency applied by generator 24 and the resonant frequency of filter 42 when the system is first started. However, any such mismatch is corrected by tuning circuit 120. At startup, switch 124 connects digital-to-analog converter 126 to filter 128 and hence to control input 25 of the generator. As further discussed below, microprocessor 74 receives a baseband signal through analog-to-digital converter 72. The amplitude of this signal is directly related to the amplitude of the signals passing through filter 40 and through amplifiers 62 and 64. By returning a feedback signal through converter 126 to control input 25, the microprocessor adjusts the first or red carrier frequency supplied by generator 24 to maximize the amplitude of the signals passing through filter 42. This maximum occurs when the red carrier frequency is substantially equal to the resonant frequency of filter 42 and hence within the passband of the filter. At this point, the microprocessor actuates switch 124 to connect phase detector 122 with control input 25 via filter 128, and to disconnect converter 126. The signal from the phase detector represents the phase shift caused by filter 42. The phase shift signal applied to the control input of generator 24 causes further adjustment of the red carrier frequency, until the phase shift is reduced to zero. This zero phase shift or "phase lock" condition occurs when the red carrier frequency applied by generator 24 is precisely equal to the resonant frequency of filter 42. Thus, the phase shift signal provides a final, precise turning of the red carrier frequency to the resonant frequency of the filter. The tuning circuit maintains phase lock, with continued feedback of the phase shift signal from detector 122, during continued operation.

Tuning circuit 130 acts in substantially the same way to adjust the second or IR carrier frequency applied by generator 28 to match the resonant frequency of filter 52, and to maintain the IR carrier frequency signal in "phase lock" with the output signal from filter 52. Thus, in steady state operation, each carrier frequency is precisely matched to the resonant frequency of one of the filters. As the resonant frequency of each filter lies at the center of the filter's passband, each carrier frequency lies within the passband of one filter. In this steady state condition the signal from filter 42 applied to amplifier 62 consists essentially of the signal component at the first carrier frequency, representing the red wavelength transmissivity. Conversely, the signal component passing through second filter 52 to amplifier 88 consists essentially of the signal component at the second carrier frequency, representing the infrared transmissivity of the fingertip. The filter network 40 thus serves both to reject the spurious ambient light and electromagnetic interference components and also to separate the two carrier frequency signals from one another.

As indicated by curve $F_1$, the separated, amplified signal as fed into the first signal processing channel 86 through amplifiers 62 and 64 has amplitude varying in accordance with the varying red wavelength transmissivity of the fingertip, i.e., it is a signal at the first carrier frequency amplitude-modulated with the red wavelength transmissivity. Demodulator 66 recovers the base band or information content of this modulated signal and passes the base band signal through low pass filter 70. Low pass filter 70 removes residual carrier frequency or noise component and smoothes the base band signal to provide a varying base band signal voltage as indicated by curve $BB_R$. The base band signal voltage $BB_R$ represents the red wavelength transmissivity of the fingertip. This signal has a DC component and an AC component at a frequency equal to the patient's pulse frequency or heart rate, viz., typically about 1–2 Hz, and never more than about 5 Hz (300 beats/min.).

Analog to digital converter 72 provides digital representations of the red transmissivity signal $BB_R$ to microprocessor 74. As indicated by curve $BB_R$, the AC component or variation with time in the red transmissivity is typically much smaller than the DC component. Therefore, each digital representation or value delivered by analog to digital converter 72 to microprocessor 74 provides a reasonable approximation of the DC component of transmissivity at the red wavelength. Moreover, microprocessor 74 is arranged to perform a digital low pass filtering or averaging on successive values captured through analog to digital converter 72, so as to derive a more accurate value for the DC component of red wavelength transmissivity.

The base band red wavelength transmissivity signal is also delivered to high pass filter 76, which effectively strips the DC component from the signal and passes only the AC component to channel amplifier 78. After amplification in the channel amplifier and further filtering by low pass filter 80 to remove stray noise components and the like, the amplified AC component passes to sample and hold unit 82. Sample and hold unit 82 is actuated by microprocessor 74 to sample the AC signal at a sampling rate of about 25–30 Hz or more, and to deliver successive samples to analog to digital converter 84. The analog to digital converter delivers a stream of successive digital representations or values each representing one sample of the AC component. The microprocessor is arranged to calculate the AC component or peak to peak value of the red transmissivity signal from the successive values.

In exactly the same way, the amplitude-modulated signal $F_2$ at the second carrier frequency representing IR transmissivity is delivered by filter 52 through amplifiers 88 and 90. This signal is processed by the second signal processing channel 92 to recover the base band infrared transmissivity signal $BB_{IR}$ and further processed in microprocessor 74 to recover the AC and DC components of this signal.

Microprocessor 74 is arranged to calculate the oxygen saturation of the blood within fingertip 16 according to the formula:

Oxygen Saturation $= AR^2 + BR + C$ where:

$$R = \frac{(AC_R/AC_{IR})}{(DC_R/DC_{IR})}$$

$AC_R$ and $DC_R$ are the AC and DC components, respectively, of the red transmissivity signal;

$AC_{IR}$ and $DC_{IR}$ are the AC and DC components respectively of the infrared transmissivity signal; and A, B and C are constants determined by empirical curve fitting in design of the system, against the results of standard blood oxygen determinations.

The oxygen saturation calculated by microprocessor 74 is displayed on display unit 110. As will be appreciated, apparatus in accordance with the present invention may also include other well known features commonly found in oximeters as, for example, testing devices for checking operation of the system and devices for deriving information concerning the presence or absence of a pulse and the pulse rate from one or both of the baseband transmissivity signals. The microprocessor can be programmed to detect the pulse rate by monitoring peaks in the AC component of the red transmissivity signal supplied by channel amplifier 78, as by monitoring the sequence of digital representations delivered through analog to digital converter 84. As set forth in U.S. Pat. No. 4,407,290, the levels of more than one constituent in the blood may be detected by using light at three or more different wavelengths. That technique may be employed according to the present invention. A separate carrier frequency would be utilized for each of these different wavelengths, i.e., three different carrier frequencies for three different wavelengths to detect the levels of two different constituents.

Microprocessor 74 controls the gains of amplifiers 64, 78, 90 and 104 to maintain the signals supplied to each analog to digital converter 72, 84, 98 and 100 within the optimum operating range of the converter. For example, if the digital values or representations applied by converter 72 indicate that the signal voltage applied to this converter is approaching or exceeding the operating range of the converter, microprocessor 74 will apply an appropriate feedback signal to amplifier 64 to reduce the gain of that amplifier. Conversely, if the digital values supplied by converter 84 indicate that the signals arriving at that converter are at or below the minimum operating voltage of the converter, the microprocessor will increase the gain of amplifier 78. The microprocessor keeps track of the gain adjustments made with respect to each amplifier and applies appropriate multipliers to the digital values supplied through each digital converter. For example, as the gain of amplifier 64 is increased, the multiplier applied to the values from converters 72 and 84 will be decreased. Thus, the microprocessor will obtain accurate values for the AC and DC components of the various transmissivity signals despite changes in the gains of the amplifiers.

The carrier frequencies utilized in apparatus and methods according to the present invention should, desirably, be far above the fundamental flicker frequency of the ambient lighting, and above the harmonics of the flicker frequency. However, it is desirable to maintain the carrier frequencies below the frequencies predominating in electromagnetic interference such as the interference caused by electrosurgical equipment. Carrier frequencies between about one KHz and about ten KHz are preferred. The carrier frequencies must differ from one another by an amount sufficient to permit separation of the respective signals according to the carrier frequencies. The necessary separation in turn will depend upon the bandwidth of the filters. Although relatively narrow filter bandwidths are desirable for signal separation and interference rejection, there is a lower bound on filter bandwidth set by phase distortion considerations. Each filter should pass signals within about ±15 Hz of the associated carrier frequency, without substantial phase error. For a phase error of less than about 1° over this ±15 Hz range using inductive-capacitive networks as shown, the half-power bandwidth of each filter should desirably be about 1.7 KHz or more, assuming that each carrier frequency is accurately matched to the resonant frequency of the associated filter. With the continuous phase lock tuning used in the preferred embodiments discussed above, this assumption is justified.

The waveform of the carrier frequency signal, and hence the waveform of the power applied to each LED, most preferably is sinusoidal. Other waveforms have significant harmonic components. The harmonic components of one carrier frequency may fall within the passband of the filter associated with the other carrier frequency, and hence may cause errors.

Numerous variations and combinations of the features set forth above can be utilized without departing from the invention as defined by the claims. For example, the photodetector may be arranged to operate in a photovoltaic or photoamperic mode, and hence the photodetector bias supply 36 shown above may be eliminated. Also, the center node 50 of the filter network may be grounded. Filters of configurations other than that shown may be utilized.

In a variant of the tuning arrangement, the filters 42 and 52 may be provided with variable resistors in place of the fixed resistors 48 and 58. These may be set at startup to provide a broad bandwidth, and adjusted to the normal value under control of the microprocessor once the system is in phase lock. In this arrangement, the digital-to-analog converters 126 and 136 may be omitted. In a less preferred arrangement, tuning can be accomplished without phase lock, as by amplitude maximization alone. Also, the tuning circuits can operate by adjusting the resonant frequencies of the filters rather than the carrier frequencies. The result—precise matching of carrier and resonant frequencies—is the same. In a less preferred variant, the tuning circuitry can be omitted, provided that the filters are built to very close tolerances to provide an acceptable match between carrier and resonant frequencies.

In the embodiment discussed above, the filters serve both to separate the two carrier frequency signals and also to reject interference upstream of the front end amplifiers 62 and 88. In a less preferred embodiment, the photodetector signal could be amplified prior to separation, as by connecting the photodetector to a single front end amplifier and delivering the output signal from the front end amplifier to a filter network substantially as discussed above. According to the broad compass of the invention, it is not essential to employ analog domain filters. Thus, the components of the photodetector signal can be separated from one another according to their frequencies by digital filtering techniques. As these and other variations and combinations of the features described above can be utilized without departing from the present invention as defined in the claims, the foregoing description of the preferred embodiments should be taken by way of illustration rather than by way of limitation of the invention as defined in the claims.

I claim:

1. Apparatus for monitoring the level of a constituent of the blood within a body structure comprising:
    (a) illumination means for emitting light at a plurality of wavelengths and directing the emitted light through said body structure;
    (b) photodetector means for detecting light from said illumination means transmitted through said body structure and producing at least one photodetector signal representing the intensity of said detected light;
    (c) carrier frequency means for varying the amplitude of the light at each said wavelength emitted by said illumination means at a different carrier frequency whereby said at least one photodetector signal will include a component at each said carrier frequency bearing information relating to the optical transmissivity of said body structure at one of said wavelengths;
    (d) separation means for subdividing said at least one photodetector signal by frequency so as to separate said components at said different carrier frequencies from one another; and
    (e) interpretation means for determining the level of said constituent from said separated components.

2. Apparatus as claimed in claim 1 wherein said separation means includes a plurality of filters each associated with one of said carrier frequencies, each said filter being arranged to pass signal components at the associated carrier frequency and to reject signal components at all other ones of said carrier frequencies.

3. Apparatus as claimed in claim 2 wherein each of said filters has a finite pass band encompassing the associated carrier frequency, and wherein each of said filters is arranged to provide a filtered signal consisting essentially of the signal components within the pass band.

4. Apparatus as claimed in claim 3 further comprising tuning means for adjusting said carrier frequency means or said filters to bring said carrier frequencies within said passbands.

5. Apparatus as claimed in claim 4 wherein each said filter has a resonant frequency within its passband, and wherein said tuning means includes means for adjusting said carrier frequency means or said filters to match said carrier frequencies with said resonant frequencies.

6. Apparatus as claimed in claim 5 wherein said tuning means includes means for detecting phase shift in each said filter and adjusting said carrier frequency means or said filters to minimize said phase shift.

7. Apparatus as claimed in claim 3, further comprising amplification means for separately amplifying each of said filtered signals, said filters being connected to said photodetector means without intervening amplification.

8. Apparatus as claimed in claim 1 wherein said illumination means is operative to provide illumination at all of said wavelengths simultaneously, whereby said at least one photodetector signal will include components at all of said frequencies simultaneously.

9. Apparatus as claimed in claim 8 wherein said interpretation means includes a separate signal processing channel associated with each of said wavelengths, said separation means including means for routing the component of said photodetector signal at each said carrier frequency to a different one of said signal processing channels, and wherein each said signal processing channel includes means for demodulating the signal component directed to such signal processing channel to recover a transmissivity signal representing the transmissivity of said body structure at the associated one of said wavelengths.

10. Apparatus as claimed in claim 9 wherein said interpretation means includes means for determining the AC and DC components of said transmissivity signals and computing the level of said constituent from said AC and DC components.

11. Apparatus as claimed in claim 10 wherein said separation means includes a plurality of filters, each associated with one of said carrier frequencies, each said filter being arranged to pass signal components at the associated carrier frequency and to reject signal components at all other ones of said carrier frequencies, each said filter being connected to one of said signal processing channels so that signals passed through each said filter will be supplied to the signal processing channel connected therewith.

12. Apparatus as claimed in claim 11 further comprising a front end amplifier connected between each said filter and the associated signal processing channel.

13. A method of monitoring the level of a constituent of the blood within a body structure comprising the steps of:

(a) emitting light at a plurality of wavelengths while varying the amplitude of the emitted light of each said wavelength at a different carrier frequency and directing the emitted light through said body structure;

(b) detecting light from said illumination means transmitted through said body structure and producing at least one photodetector signal representing the intensity of said detected light whereby said at least one photodetector signal will include a component at each said carrier frequency bearing information relating to the optical transmissivity of said body structure at one of said wavelengths;

(c) subdividing said at least one photodetector signal by frequency so as to separate components at said different carrier frequencies from one another; and (d) determining the level of said constituent from said separated components.

14. A method as claimed in claim 10 wherein said subdividing step is performed by passing said at least one photodetector signal into a plurality of filters so that each said filter passes signal components at one of said carrier frequencies and rejects signal components at all other ones of said carrier frequencies.

15. A method as claimed in claim 11 wherein each said filter has a finite pass band encompassing the carrier frequency associated with that filter, the method further comprising the step of rejecting signal components outside of the pass band of each said filter to provide a filtered signal from each said filter consisting essentially of the signal components within the pass band of that filter.

16. A method as claimed in claim 15 further comprising the step of adjusting said carrier frequencies or the pass bands of said filters to bring each carrier frequency within the pass band of the associated filter.

17. A method as claimed in claim 16 wherein said at least one photodetector signal is delivered to said filters without amplification, the method further comprising the step of amplifying each said filtered signal.

18. A method as claimed in claim 13 wherein said light emitting step includes the step of emitting light of all of said wavelengths simultaneously.

19. A method as claimed in claim 13 wherein said determining step includes the steps of demodulating each of said amplified filtered signals to recover a base band signal representing transmissivity of said body structure at one of said wavelengths, and determining the AC and DC components of each said base band signal.

* * * * *